(12) United States Patent
Chen et al.

(10) Patent No.: US 10,470,647 B2
(45) Date of Patent: *Nov. 12, 2019

(54) SURGICAL TISSUE PROTECTION SHEATH

(71) Applicant: SPIWay LLC, Carlsbad, CA (US)

(72) Inventors: Eugene Chen, Carslbad, CA (US); Aylin Kim, Seattle, WA (US); Cang Lam, Irvine, CA (US); Blake Hannaford, Seattle, WA (US); Randall A. Bly, Seattle, WA (US); Jeremy Ciporen, Carlsbad, CA (US); Kristen Moe, Carlsbad, CA (US); Louis Kim, Carlsbad, CA (US); Laligam Sekhar, Carlsbad, CA (US)

(73) Assignee: SPIWay LLC, Carlsbad, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 15/933,036

(22) Filed: Mar. 22, 2018

(65) Prior Publication Data

US 2018/0206709 A1    Jul. 26, 2018

Related U.S. Application Data

(63) Continuation of application No. 15/340,718, filed on Nov. 1, 2016, now Pat. No. 9,949,621, which is a (Continued)

(51) Int. Cl.
*A61B 1/32* (2006.01)
*A61B 1/00* (2006.01)
(Continued)

(52) U.S. Cl.
CPC ............ *A61B 1/00154* (2013.01); *A61B 1/32* (2013.01); *A61B 17/00234* (2013.01); *A61B 17/24* (2013.01); *A61B 17/29* (2013.01); *A61B 17/3423* (2013.01); *A61B 90/00* (2016.02); *A61B 17/3431* (2013.01); *A61B 90/39* (2016.02); *A61B 2017/00278* (2013.01); *A61B 2017/00849* (2013.01);
(Continued)

(58) Field of Classification Search
CPC ........... A61B 90/02; A61B 90/00; A61B 1/32; A61B 17/3431; A61B 2017/3433; A61B 2017/3429; A61B 2017/345
See application file for complete search history.

(56) References Cited

U.S. PATENT DOCUMENTS 6,607,546 B1 * 8/2003 Murken ........... A61B 17/12104
606/196
7,730,888 B2 * 6/2010 Dunlap ............. A61M 16/0461
128/207.18
(Continued)

*Primary Examiner* — Jacqueline T Johanas
(74) *Attorney, Agent, or Firm* — Perkins Coie LLP; Kenneth H. Ohriner

(57) ABSTRACT

A surgical sheath for use in endoscopic trans-nasal or intra-ocular surgery has an angle section joined to a conical section, with the conical section having a central axis not parallel to a central axis of the angle section. A body section is joined to the angle section, with the body section having a length at least twice the length of the angle section. The conical section, the angle section and the body section may be a flexible or compliant material. The sheath reduces collateral trauma to the tissues in the surgical pathway.

16 Claims, 9 Drawing Sheets

Related U.S. Application Data continuation of application No. 14/626,184, filed on Feb. 19, 2015, now abandoned, which is a continuation of application No. 13/798,990, filed on Mar. 13, 2013, now Pat. No. 8,986,201.

(60) Provisional application No. 61/730,588, filed on Nov. 28, 2012.

(51) Int. Cl.

| | |
|---|---|
| *A61B 17/00* | (2006.01) |
| *A61B 90/00* | (2016.01) |
| *A61B 17/24* | (2006.01) |
| *A61B 17/34* | (2006.01) |
| *A61B 17/29* | (2006.01) |
| *A61B 90/30* | (2016.01) |
| *A61M 1/00* | (2006.01) |

(52) U.S. Cl.
CPC .......... *A61B 2017/00876* (2013.01); *A61B 2017/2926* (2013.01); *A61B 2017/345* (2013.01); *A61B 2090/08021* (2016.02); *A61B 2090/306* (2016.02); *A61B 2217/005* (2013.01); *A61B 2217/007* (2013.01); *A61M 1/0084* (2013.01)

(56) References Cited

U.S. PATENT DOCUMENTS

| | | | | |
|---|---|---|---|---|
| 8,986,201 | B2* | 3/2015 | Chen | A61B 17/3423 600/201 |
| 9,451,981 | B2* | 9/2016 | Chen | A61B 17/3423 |
| 10,172,639 | B2 | 1/2019 | Payne | |
| 2005/0240147 | A1* | 10/2005 | Makower | A61B 17/24 604/96.01 |
| 2006/0287583 | A1* | 12/2006 | Mangiardi | A61B 17/02 600/208 |
| 2007/0191876 | A1* | 8/2007 | Dubrul | A61F 5/56 606/199 |
| 2010/0174308 | A1* | 7/2010 | Chang | A61B 17/24 606/199 |
| 2011/0048430 | A1* | 3/2011 | Arnon | A24F 47/00 128/848 |
| 2011/0118551 | A1* | 5/2011 | Ciporen | A61B 17/3423 600/201 |
| 2012/0203069 | A1* | 8/2012 | Hannaford | A61B 17/3423 600/201 |
| 2015/0209074 | A1* | 7/2015 | Payne | A61B 17/3423 600/114 |

* cited by examiner

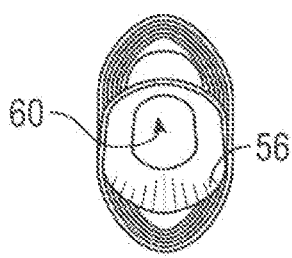
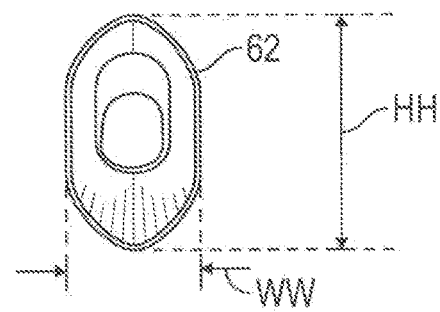
FIG. 4    FIG. 5
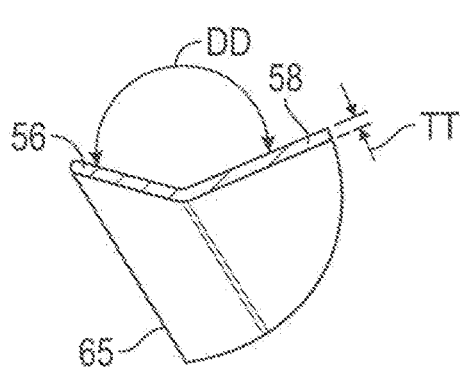
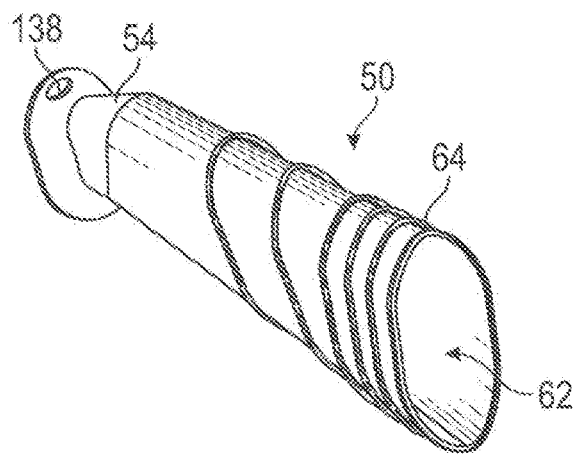
FIG. 6    FIG. 7
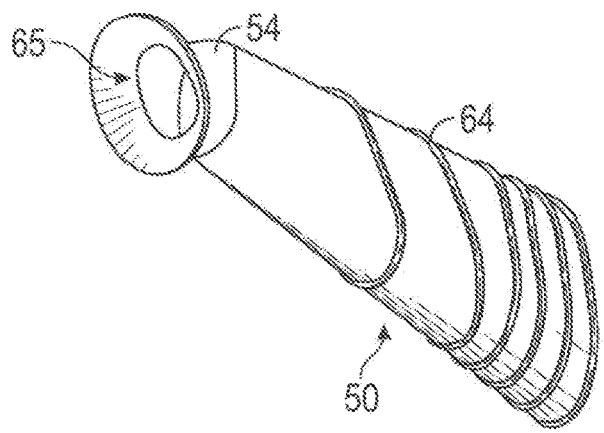
FIG. 8

US 10,470,647 B2

SURGICAL TISSUE PROTECTION SHEATH

This application is a Continuation of U.S. patent application Ser. No. 15/340,718 filed Nov. 1, 2016 and now pending, which is a Continuation of U.S. patent application Ser. No. 14/626,184, filed Feb. 19, 2015, and now abandoned, which is a Continuation of U.S. patent application Ser. No. 13/798,990, filed Mar. 13, 2013, and now issued as U.S. Pat. No. 8,986,201, which claims priority to U.S. Provisional Patent Application No. 61/730,588 filed Nov. 28, 2012. Each of the applications listed above is incorporated herein by reference.

BACKGROUND OF THE INVENTION

Endoscopic surgery within the head is a common procedure in neurological surgery and otolaryngology. It avoids large cranial incisions and can reduce the need brain retraction and prolonged wound healing. Endoscopic surgery within the head also provides improved illumination and visualization of the target tissues because the camera of the endoscope is brought directly to the surgical site.

During this type of surgery, there may be local trauma to the tissues in the surgical pathway, resulting from pressure or abrasion caused by the surgical instruments. Generally these tissues are the nasal mucosa, turbinates, nasal septum, and sphenoid/frontal/maxillary sinus. When transorbital approaches are used, orbital and periorbital tissue are subject to local trauma. Surgical pathway trauma can add to the trauma of the procedure and prolong the patient's recovery time. Liquids in the surgical pathway, such as mucous, blood, and soiled irrigation fluid, tend to obscure the view of the endoscope. This leads to the constant need for irrigation and suction of the obstructing liquids. In some cases the endoscope may also have to be removed, cleaned and replaced multiple times during a single procedure. This disadvantage tends to increase the complexity and time requirements of the operation. In addition, with each movement of a surgical tool into or out of the surgical pathway, the surrounding tissues are put at risk of additional trauma. Improved devices and methods are therefore needed.

BRIEF DESCRIPTION OF THE DRAWINGS

In the drawings, the same reference number indicates the same element in each of the views.

FIG. 4 is left end view of the sheath of FIG. 1.
FIG. 5 is a right end view of the sheath of FIG. 1.
FIG. 6 is an enlarged detail view of detail A shown in FIG. 3.
FIG. 7 is front, top and right side perspective view of the sheath shown in FIG. 1.
FIG. 8 is rear, bottom and right side perspective view of the sheath shown in FIG. 1.

DETAILED DESCRIPTION OF THE DRAWINGS

Figure 1:
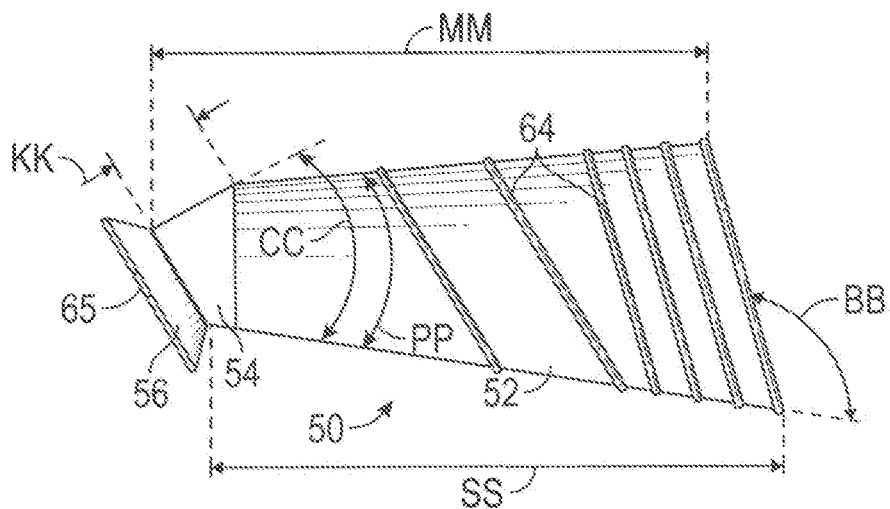
FIG. 1 is a side view of a tissue protection sheath.

FIGS. 1-8 show a first design for a sheath 50 having a body section 52, and angle section 54 and a flare or conical section 56. The sheath 50 may be molded of rubber or plastic as a one piece unit with the body section 52, the angle section 54 and the flare section integrally joined together. As shown in FIG. 6, the sheath 50 may have a thin flexible wall 58 having a thickness TT which allows the sheath to conform to the surgical space, or the inner wall of the patient's nostrils. The flare section 56 may be provided as a conical ring forming an angle DD of 120-160 or 130-150 degrees with the top wall of the angle section. The sheath 50 may have a single through passageway 60 extending from a distal opening 62 to a proximal opening 65. As shown in FIGS. 4, 5 and 8, the openings 62 and 65, and the cross section of the body 52, may be generally in the shape of an oval or an ellipse.

Figure 3:
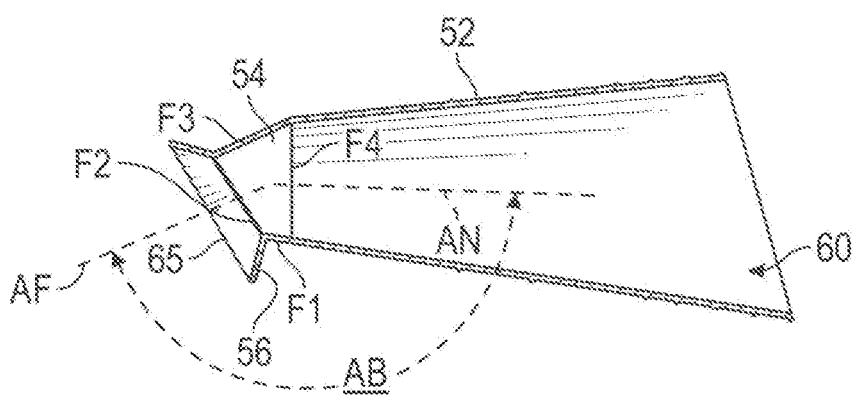
FIG. 3 is a section view of the sheath shown in FIG. 1.

Referring to FIGS. 1 and 3, the distal opening 62 may lie in a plane forming an angle forming an angle BB with the bottom of the sheath, with BB ranging from 95 to 125 or 100 to 115 degrees. As best shown in FIG. 3, the angled section 54 may be described as joined to the body section 52 at a vertical line 51. The upper and lower walls of the sheath extend distally away from the vertical line 51 towards the distal opening 62 at acute angles to the line 51, which may the same or different angles. As shown in FIG. 1, the included angle CC between the top surface of the angled section 54 and the lower wall of the body section may range from 25 to 40 or 30 to 35 degrees. The angle PP in FIG. 1 relating to the diverging angle of the top and bottom surfaces of the body section is typically 10-20 or 12-16 degrees. Dimension KK may be 8-16 or 10-14 mm, with dimensions MM and SS both generally about 65-85 or 70-80 mm.

For some procedures the sheath 50 may be provided as a cut-to-length unit. For example, the sheath may be provided in a sterile package, and have a length up to about 100 mm, with the surgeon cutting off a section of the front or distal end 62, to obtain a desired length. Scale markings (inches or millimeters) may optionally be printed or molded on an outside surface of the sheath for this purpose.

Figure 2:
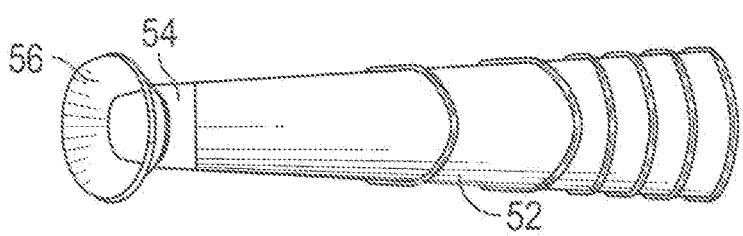
FIG. 2 is a bottom view of the sheath shown in FIG. 1.

Turning to FIGS. 1-2 and 7-8, one or more ridges 64 may be provided on an outer surface of the body section 52. The ridges 64 may project up by 0.5 to 3 mm above the nominal outer surface of the sheath 50. A cluster of 2-5 ridges 64 may be provided near the distal opening 52, as shown in FIGS. 1 and 2. These ridges 64 may be parallel to each other, and optionally also parallel to the plane of the distal opening 52. Additional ridges 64, oriented at an angle of e.g., 10-20 or 13-17 degrees, may be provided more centrally on the body section 52 of the sheath 50. The ridges may optionally be provided as rings extending continuously around the outside surface of the body section.

Optionally, one or more spring or elastic elements 66, such as a spring wire 66, may be attached to or embedded in the sheath 50, to help expand the sheath from a folded or collapsed position into and expanded deployed position, after the sheath is positioned in the surgical pathway. The elastic element 66 may be a Nitinol wire. The dimensions and angles shown in the drawings of all embodiments may typically be varied by 10, 20 or 30% depending on various design parameters.

The angle section 54 may allow the proximal end of the sheath 50 to be more easily stretched and/or deflected. This allows for more versatile movement of surgical instruments extending through the sheath during surgery. As shown in FIGS. 1 and 3, the angle section 54 forms an irregular quadrilateral shape in cross section. In FIG. 3, the angle section 54 may be defined by line F4 along with segments or lines F1, F2 and F3, with F4 and F2 forming a first acute angle and with F1 and F3 forming a second acute angle. Each of the sides or segments F4, F1, F2 and F3 forming the angle section 54 may also have different lengths. F3 may be substantially perpendicular to F2. The angle section 54 may alternatively be described via a centerline AN perpendicular to and bisecting segment or line F4 and intersecting a centerline AF of the conical section 54 at an angle AB of 5-30 or 10-20 degrees.

The wall thickness of the sheath 50 may be thinner at the proximal end adjacent to the flare 56, to allow the proximal end to more easily stretch. For example, the sheath 50 shown in FIGS. 1-8 may be 6 to 10 cm long with the proximal 10 to 30% of the length having a reduced wall thickness in comparison to the rest of the sheath. The wall thickness of this section may be 20 to 80 or 30 to 70% of the regular wall thickness of the rest of the sheath. The wall thickness may optionally be largely uniform with all sections of the sheath having a similar thickness TT.

Figure 12:
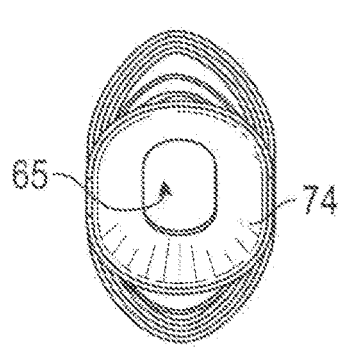
FIG. 12 is left end view of the sheath of FIG. 9.
Figure 13:
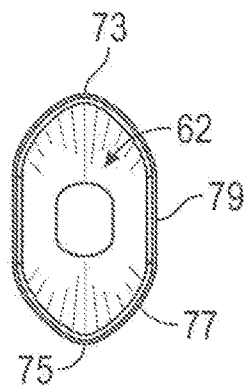
FIG. 13 is a right end view of the sheath of FIG. 9.
Figure 14:
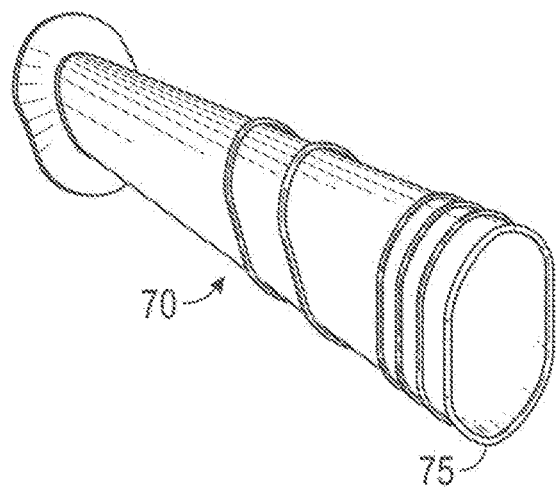
FIG. 14 is front, top and right side perspective view of the sheath shown in FIG. 9.

FIGS. 9-15 show a second design 70 similar to the sheath 50 but without the angle section 54. As with the sheath 50, the sheath 70 may have distal and proximal openings oriented in non-parallel planes. The sheath 70 may have a flare end 74 that is flatter than the flare end 56 on the sheath 50, with the flare end 74 at an angle EE to the centerline of 50 to 70 or 55 to 65 degrees, and with angle FF typically ranging from 8 to 15 degrees. The outer diameter GG of the flare end 74 may be 22-30 or 24-28 mm, with the outer diameter of the front end generally about 16-22 mm. The sheath 70 may also have a longer and narrower through passageway, as shown in FIG. 12. Comparing FIG. 13 to FIG. 3 shows that the body section of the sheath 70 may be symmetrical about the centerline 71 while the body section of the sheath 50 is not similarly symmetrical.

Figure 9:
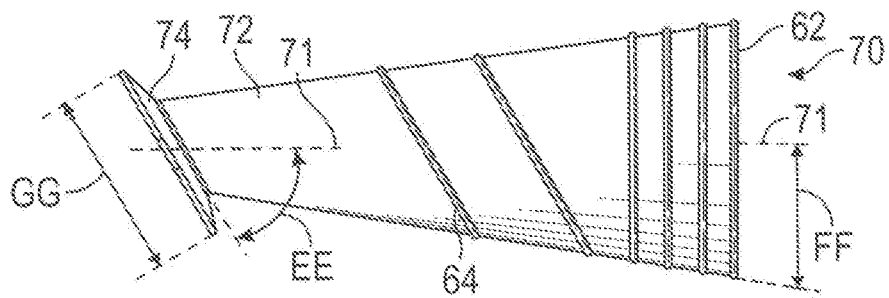
FIG. 9 is a side view of a second embodiment of a tissue protection sheath.
Figure 10:
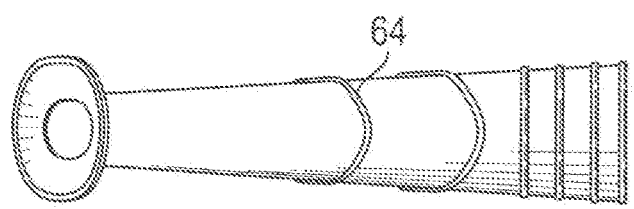
FIG. 10 is a bottom view of the sheath of FIG. 9.
Figure 11:
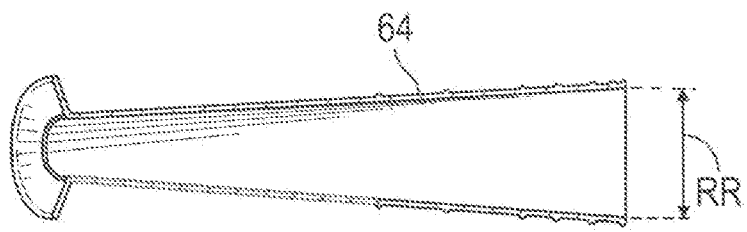
FIG. 11 is a centerline section view of the sheath of FIG. 9.
Figure 15:
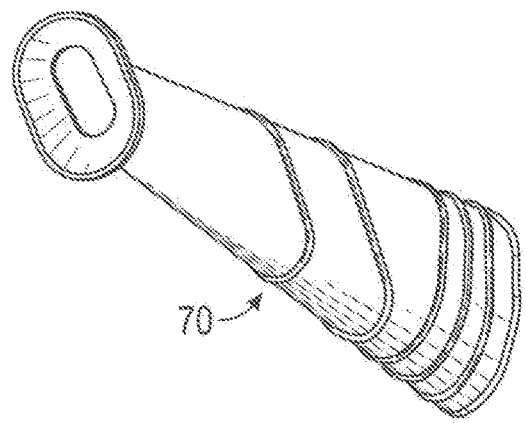
FIG. 15 is rear, bottom and right side perspective view of the sheath shown in FIG. 9.
Figure 16:
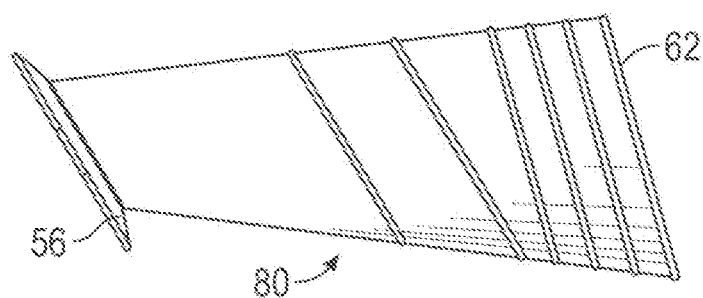
FIG. 16 is a side view of a third embodiment of a tissue protection sheath.
Figure 17:
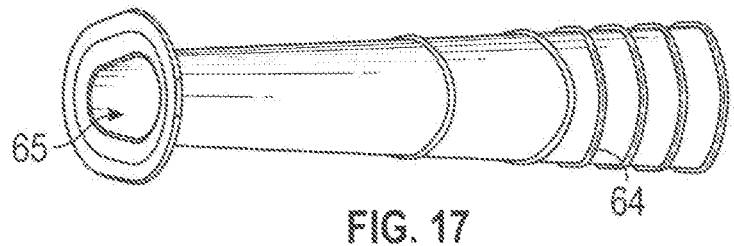
FIG. 17 is a bottom view of the sheath shown in FIG. 9.
Figure 18:
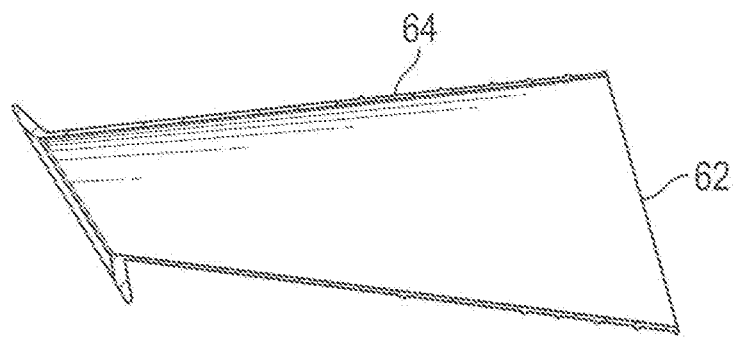
FIG. 18 is a section view of the sheath of FIG. 16 taken along a centerline.

As shown in FIGS. 9 and 13, the body section of the sheath 70 and/or the distal opening 62 may have upper and lower creases 73 and 75 having a radius of 2 mm or less, with curved sidewalls 77 leading from the creases to a substantially flat center sidewall 79. As shown in FIGS. 12 and 15, the proximal opening 65 may be an oval.

Figure 19:
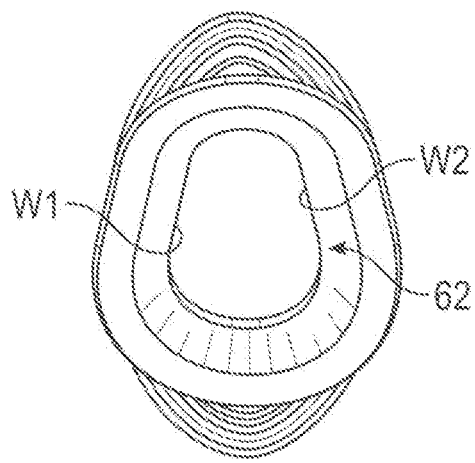
FIG. 19 is left end view of the sheath of FIG. 15.
Figure 20:
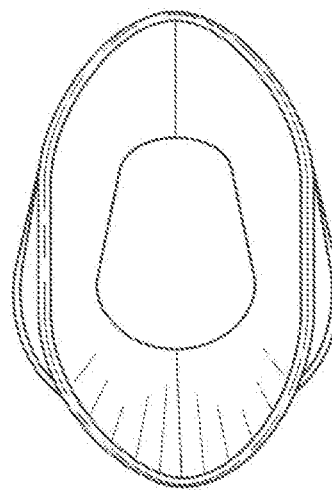
FIG. 20 is a right end view of the sheath of FIG. 15.
Figure 21:
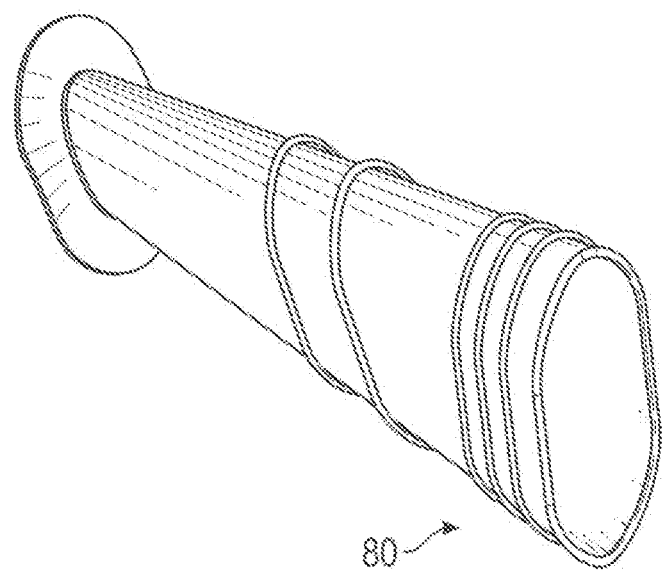
FIG. 21 is front, top and right side perspective view of the sheath shown in FIG. 15.
Figure 22:
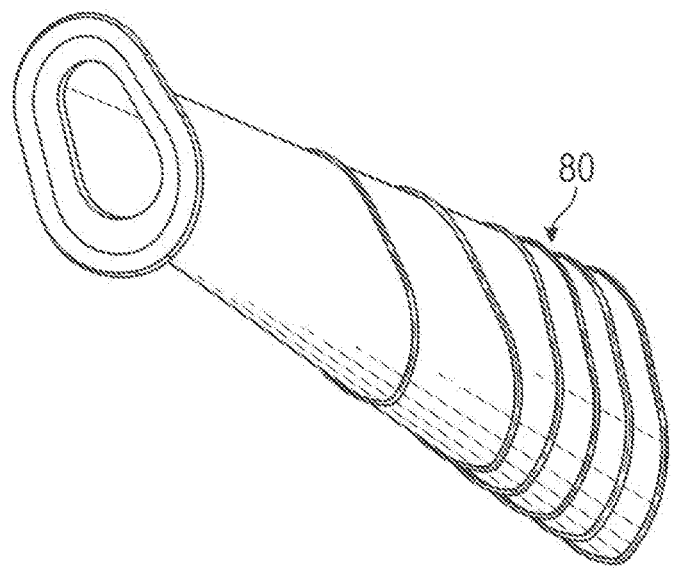
FIG. 22 rear, bottom and right side perspective view of the sheath shown in FIG. 15.

FIGS. 16-22 show a third design 80 that is similar to the sheath 70 but having a distal opening 62 in a plane forming an acute angle with a longitudinal centerline of the body section, similar to FIG. 1, as opposed to the perpendicular distal opening orientation in FIG. 9. As shown in FIG. 19 the proximal opening 62 may have non-parallel sidewalls upwardly converging sidewalls W1 and W2 joined by a smaller radius of curvature at the top and a larger radius of curvature at the bottom, in the form of a teardrop or an uneven oval. In each of the sheaths described, the body section may be at least 2, 4, 6, 8 or 10 times longer than the conical section, or the combined length of the conical section and the angle section, if used.

Figure 23:
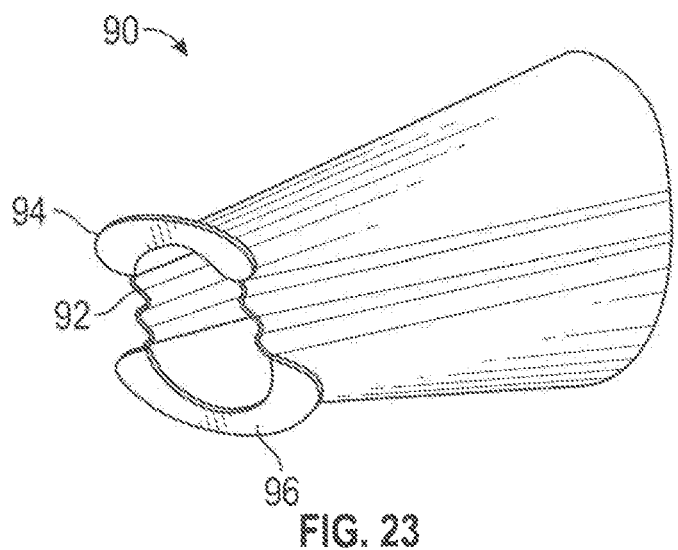
FIG. 23 is rear, top and right side perspective view of another sheath design.

FIG. 23 shows a similar design further including pleats or folds 92 at the proximal end. The flare end may also be split into an upper section 94 and a lower section 96, with no flare section overlying the pleats 92. This allows the proximal end of the sheath 90 to more easily stretch open to better accommodate manipulation of surgical tools. The pleats 92 may be molded into the proximal end of the sheath 90, with the pleats reducing and blending into the body section of the sheath towards the distal end of the sheath 90. The wall thickness at the pleats may be reduced to e.g., 0.2-0.7 mm, to allow the pleats to stretch with nominal force.

Figure 24:
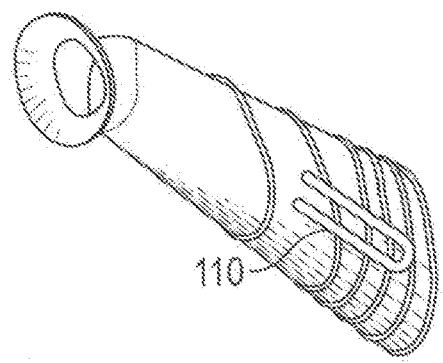
FIG. 24 rear, top and right side perspective view of a sheath similar to the sheath of FIG. 1 and further including side pockets.

FIG. 24 shows a sheath which may be similar or the same as the sheaths 50, 70 or 80, and further including pockets 110 on opposite sides configured to accept the jaws of a bayonet forceps. The pockets may help the forceps to grasp and hold the sheath, and also allow the sheath to be pushed forward using the forceps, but without excessively clamping or squeezing the sheath.

Figure 25:
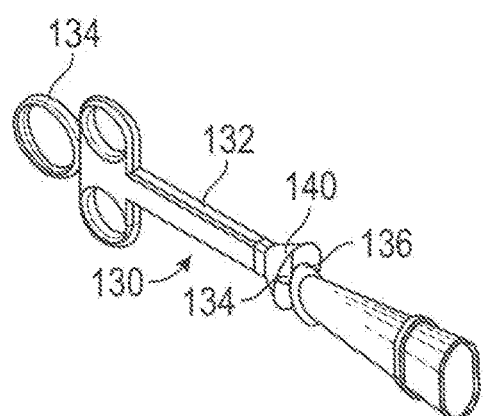
FIG. 25 is a side view of a sheath delivery tool.

FIG. 25 shows a sheath deployment tool 130 that may be used to deploy a sheath. The tool 130 has a plunger 134 slidable into a handle 132. A hook 136 or other grasping feature on the plunger 134 engages a hook slot 138 on the sheath, with the hook slot 138 shown in FIG. 1. Funnel guides 140 may be provided on the handle 132 to collapse down and guide the sheath into the handle. The tool 130 may then be used to place the sheath into a surgical pathway.

Figure 26:
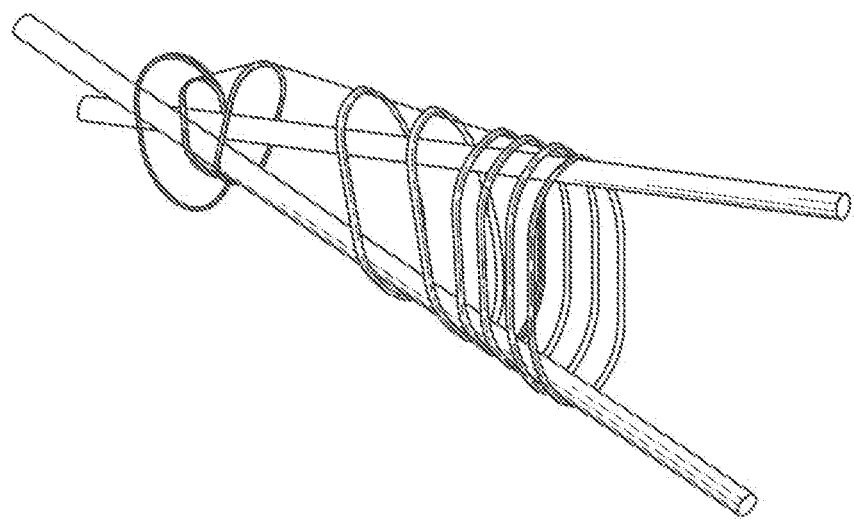
FIG. 26 is a rear, top and right side perspective view of the sheath of FIG. 1 with surgical instruments schematically illustrated in use.
Figure 27:
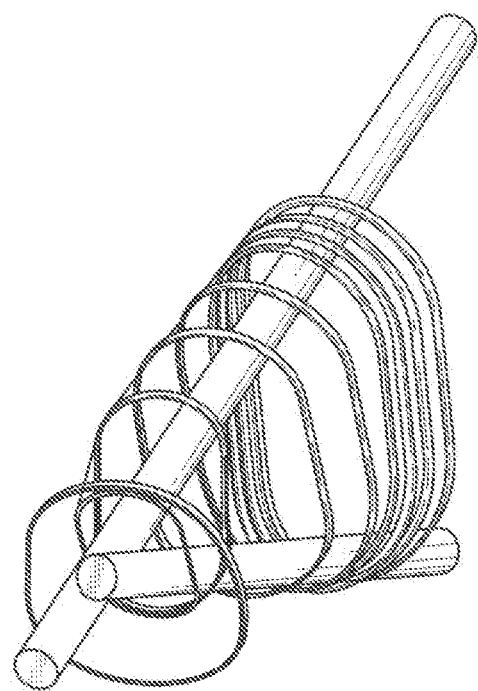
FIG. 27 is a front, top and right side perspective view of the sheath and surgical instruments as shown in FIG. 26.

FIGS. 26 and 27 show two surgical tools in use with the sheath. As the sheath tapers outwardly from the proximal opening 65 to the distal opening 62, clashing of the instruments may be reduced as the sheath provides more room for the instruments to move at a distance from the leverage point of the nostril.

The sheaths described above are useful in transnasal and transorbital surgery of the head. The sheaths may also be used in other surgical procedures for protection of tissue around a surgical pathway. The sheaths above are discussed in terms of having different sections only for purposes of description. The sheaths may be manufactured from rubber or plastic as an integral one-piece unit, without specific or visible separation lines or features between the sections described.

Thus, a novel surgical sheath has been shown and described. Various changes and substitutions may of course be made without departing from the spirit and scope of the invention. The invention, therefore, should not be limited except by the following claims and their equivalents.

The invention claimed is:

1. A surgical sheath having a first end and a second end, the surgical sheath comprising:
    an angle section joined to a flare section and to a body section, the angle section having a first side, a second side, a third side, and a fourth side;

the flare section tapering inwardly from the first end of the surgical sheath to the second side of the angle section;
the second side opposite from the fourth side, and the third side intersecting and terminating at the second side;
the body section tapering outwardly from the fourth side of the angle section towards the second end of the surgical sheath, the third side not parallel to the body section and the third side forming an apex with a top surface of the body section; and
with the body section having a first length and the flare section having a second length, and with the first length greater than the second length, and with the flare section, the angle section and the body section comprising a flexible material.

2. The sheath of claim 1 further comprising one or more pleats on the body section to allow the body section to stretch outwardly more easily than the flare section.

3. The sheath of claim 1 with the body section having a wall thickness less than a wall thickness of the entire flare section.

4. The sheath of claim 1 further comprising two or more ridges on an outside surface of the body section.

5. The sheath of claim 1 with the body section having a distal opening in a plane oriented substantially perpendicular to a central axis of the body section.

6. The sheath of claim 1 with the third side extending between upper ends of the second side and the fourth side, and with the third side forming an angle of 25 to 40 degrees with a lower wall of the body section.

7. The sheath of claim 1 wherein the first side intersects and terminates at the second side, with the first side not parallel to any of the second, third and fourth sides.

8. The sheath of claim 1 wherein a central axis of the body section bi-sects the fourth side of the angle section.

9. The sheath of claim 1 wherein the flare section has a flat outer surface.

10. The sheath of claim 1 wherein the flare section tapers inwardly uniformly from the first end of the surgical sheath to the second side of the angle section.

11. The sheath of claim 1 wherein the flare section has a maximum height at the first end.

12. The sheath of claim 1 wherein the sheath has a proximal opening lying in a plane parallel to the second side.

13. A surgical sheath having a first end and a second end, the surgical sheath comprising:
a flare section joined to a first side of an angle section and a body section joined to a second side of the angle section, with the flare section, the angle section and the body section comprising a flexible material;
the body section having a bottom surface and a top surface converging towards the bottom surface at an angle PP;
the angle section having a top surface extending downward at an angle CC towards the bottom surface of the body section, so that the top surface of the angle section joins the top surface of the body section at an apex;
with the body section having a first length and the flare section having a second length, and with the first length greater than the second length;
the flare section tapering inwardly from the first end of the sheath to the angle section, and with a down-facing proximal opening of the sheath at the first end of the sheath.

14. The sheath of claim 13 wherein angle PP is 10-20 degrees and angle CC is 25 to 40 degrees so that the proximal opening is in a plane facing downward at an angle 5 to 30 degrees.

15. The sheath of claim 13 wherein the proximal opening tapers from a first width adjacent to a top end of the proximal opening to a second width adjacent to a bottom end of the proximal opening, and the second width is greater than the first width.

16. The sheath of claim 13 wherein the top surface of the body section converges uniformly along a straight line towards the bottom surface of the body section at the angle PP, from the second end of the sheath to the angle section.

* * * * *